United States Patent [19]

Kirsner

[11] Patent Number: 4,753,247
[45] Date of Patent: Jun. 28, 1988

[54] METHOD AND APPARATUS FOR MONITORING REDOX REACTIONS

[75] Inventor: Vaclav Kirsner, Westerham, England
[73] Assignee: Prutec Limited, England
[21] Appl. No.: 859,087
[22] PCT Filed: Aug. 8, 1985
[86] PCT No.: PCT/GB85/00353
     § 371 Date: Apr. 3, 1986
     § 102(e) Date: Apr. 3, 1986
[87] PCT Pub. No.: WO86/01297
     PCT Pub. Date: Feb. 27, 1986

[30] Foreign Application Priority Data

Aug. 8, 1984 [GB] United Kingdom ............... 8420116

[51] Int. Cl.$^4$ ............................................. A61B 5/05
[52] U.S. Cl. .................................. 128/734; 128/738; 324/65 P
[58] Field of Search ............... 128/734, 738; 324/65 P

[56] References Cited

U.S. PATENT DOCUMENTS

| | | | |
|---|---|---|---|
| 3,749,089 | 7/1973 | Derr | 128/738 X |
| 3,844,276 | 10/1974 | McDougall | 128/738 X |
| 3,920,003 | 11/1975 | Ash et al. | 128/738 X |
| 4,059,406 | 11/1977 | Fleet . | |
| 4,224,949 | 9/1980 | Scott et al. | 128/738 X |
| 4,498,481 | 2/1985 | Lemke | 128/734 |

FOREIGN PATENT DOCUMENTS

| | | |
|---|---|---|
| 1220540 | 5/1960 | France . |
| A2468648 | 5/1981 | France . |
| 322675 | 2/1929 | United Kingdom . |
| 525423 | 8/1940 | United Kingdom . |
| 922225 | 3/1963 | United Kingdom . |
| 1383637 | 2/1975 | United Kingdom . |
| 1395223 | 5/1975 | United Kingdom . |
| 1402677 | 8/1975 | United Kingdom . |
| 1585067 | 2/1981 | United Kingdom . |

OTHER PUBLICATIONS

Edwards, "Proposed Instrumentation . . . Impedance", Med. & Biol. Eng. & Comput., 18, 73–80, 1/1980.

Primary Examiner—Lee S. Cohen
Attorney, Agent, or Firm—Lalos & Keegan

[57] ABSTRACT

A method of monitoring changes of redox activity in a medium in vitro or in vivo which comprises placing into the medium a probe having a non-metallic surface exposed to said medium and whose surface admittance varies with the redox activity in said medium, and detecting the resulting changes in the surface admittance of said probe. The method is particularly suitable for predicting or detecting the onset of ovulation in female mammals.

12 Claims, 10 Drawing Sheets

METHOD AND APPARATUS FOR MONITORING REDOX REACTIONS

This invention relates to a method and apparatus for monitoring redox reactions, particularly but not exclusively physiological redox reactions that occur in the human or animal body, particularly those which occur during the menstrual cycle at ovulation. The invention is thus particularly concerned with a method and apparatus for detecting or predicting the onset of ovulation in mammals, and more especially in humans, and moreover an ovulation prediction or detection apparatus that is portable and is simple to use on a day-to-day basis by a completely untrained and unskilled person.

As is well known the onset of ovulation in humans and other mammals is accompanied by a number of physiological changes the monitoring of which can, with varying degrees of success, by used to detect or predict the onset of ovulation. In cattle, for example, numerous suggestions have been made for detection of oestrus by monitoring the physiological changes which take place in the vagina or in the vaginal secretions, and particularly changes in electrical resistance or conductivity of the cervical mucus. Merely as illustrative of such procedures there may be mentioned the papers published by L. B. Aizinbudas and P. P. Dovil'tis in Zhivotnovodstro 1962 (11) 68–70; Schams, Schallenberger, Hoffman and Karg in Acta Edocrinologica 86 (1977) 180–192; Heckman, Katz, Foote, Oltenaan, Scott and Marshall in J. Dairy Science 1979 (62) 64–68; Carter and Dufty in Australian Veterinary Journal 1980 (56) 321–323; Edwards in Med. & Biol. Eng. and Computing 1980 (18) 73–80; and Scipioni, Foote, Lamb, Hall, Lein and Shin in Cornell Vet. 1982 (72) 269–278; and also U.S. Pat. No. 3,844,276, U.S. Pat. No. 4,039,934 and U.S. Pat. No. 4,224,949.

So far as the prediction or detection of ovulation in humans is concerned a wide variety of approaches have likewise been tried ranging from simple physical measurements, e.g. temperature measurements, through electrometric methods to chemical and biochemical methods involving the assay of hormone levels, ATP levels etc., in various body fluids and secretions, with considerable concentration on the latter which are not suited to every day use in the home by an unskilled, untrained user.

In the electrometric field, studies have tended to concentrate on potentiometric techniques which may be suitable for carrying out on a clinical basis but which are not readily adaptable for use on an individual basis. Such potentiometric techniques for the detection or prediction of ovulation in humans are described for example in U.S. Pat. No. 3,924,609 and in Human Ovulation, Ed. C. S. Keefer, published by J. & A. Churchill Ltd. 1965 Chapter 4, pp 46–74. Studies of changes in the electrical conductivity of the squamous epithelium of the cervix uteri throughout the menstrual cycle have also been reported by Stiksa in Acta Universitatis, Carolinae Medica 1964 (10) No. 2, 139–164. So far, however, research has failed to produce a simple, safe, reliable and easy to use ovulation predictor or detector such as can be used on a day-to-day basis in the home by an unskilled, untrained user to predict or detect ovulation, and hence establish the time when the chances of a conception are the highest, either as an aid to contraception or indeed as an aid to conception.

The present invention seeks inter alia to fulfil that need and adopts an approach that is significantly different from the electrometric techniques so far investigated, namely conductimetric methods (mainly used in cattle) and potentiometric methods (mainly used in humans), and is based on changes in the physico-chemical properties of components of body tissues and fluids such as the cervical mucus. As is known, Human Ovulation, Ed. E. S. E. Hafez, published Elsevier/North Holland Biomedical Press, 1979, Chapter 19, 313–322, the physical structure of e.g. the glycoproteins (mucoproteins, mucins) changes at the time of ovulation from a highly cross-linked network of polypeptide molecules which is substantially impenetrable to spermatozoa to a striated, fibrous structure (spinnbarkeit) which can be penetrated by the sperms. Indeed, this phenomenon, i.e. the change of viscosity of the cervical mucus, has been used as an indicator of oestrus in cattle, and an instrument, an oestroscope, has been designed specifically for this purpose. It is further known that variations in the prostaglandin content of cervical mucus occur during the menstrual cycle. It is also known that during oestrus the cervical mucus undergoes an increase in water and salt content, to which is attributable also the known decrease in electrical resistance, and consequential increase in electrical conductivity, of the cervical mucus, which fact, as has already been indicated, serves as the basis of operation of the majority of electrometric oestrus detectors that are already kown, at least for veterinary applications.

The known physical changes which occur in the cervical mucus at ovulation, i.e. the changes in viscosity, rate of flow, elasticity or stretchability and crystallinity are consistent with the hypothesis that the structural changes are attributable to the reversible breaking of disulfide (—S—S—) bridges between the polypeptide molecules by an oxidation-reduction reaction representable as $$R-S-S-R + 2H^+ + 2e^- \rightleftharpoons 2RSH$$

where R represents the polypeptide. Such a reaction is accompanied by a change in redox activity or state and, while not wishing to be bound by theory, the present inventor believes that this is an example of many such reactions which are accompanied by changes in redox activity when the normal physiological functioning of an organism is disturbed e.g. at or around ovulation or during illness.

GB Pat. No. 1402677 describes a method and apparatus for monitoring ovulation usng a vaginal probe having two spaced apart electrodes for sensing the composition of vaginal fluids and developing a chosen plus or minus electrochemical potential polarity when the vaginal fluids are predominantly oxidising and an opposite electrochemical potential polarity when the vaginal fluids are predominantly reductive. The method described in GB Pat. No. 1402677 essentially requires metal electrodes and detects the potential differences between the electrodes as a result of galvanic action when they are placed in contact with the vaginal fluids. The apparatus is generally unacceptable for regular and long term use since metal ions will inevitably be released into the vaginal fluids from the electrodes with a consequent risk to the health of the subject. In addition the method and apparatus of GB Pat. No. 1402677 is generally not sufficiently sensitive, accurate and reliable.

We have now discovered an improved method and apparatus for monitoring redox activity which can be used to detect e.g. any disturbance of normal physiological functioning. For example, we have found that ovulation can be reliably and easily detected in vivo by monitoring changes in the redox activity of cervical mucus and/or tissues in the vagina using our new method and apparatus.

Thus, according to the invention there is provided a method of monitoring changes of redox activity in a medium in vitro or in vivo which comprises placing into the medium a probe having at least two non-metallic surfaces exposed to said medium and whose surface admittance varies with the redox activity in said medium, and detecting the resulting changes in the surface admittance of said probe.

In another aspect, the invention provides apparatus for monitoring changes of redox activity in vitro or in vivo which comprises a probe introducible into a medium, said probe having a non-metallic surface composed of a material whose admittance varies with the redox activity in said medium, and means for detecting any resulting changes in said surface admittance.

The term "non-metallic" is used herein to designate a material other than a metal per se but is not intended to exclude materials containing metal compounds.

The method and apparatus according to the invention are of particular applicability to the detection of ovulation. This may be achieved, in accordance with this invention, by inserting the probe into the vagina and monitoring the changes in the redox activity of the tissue or cervical mucus in the vicinity of the probe during the menstrual cycle.

As indicated above, the method and apparatus according to the invention is not limited to the monitoring of redox activities in the vagina, but is applicable to any redox reaction in almost any environment into which the probe can be introduced. In general therefore the present invention provides a method of monitoring almost any redox reaction.

In one particular arrangement the probe comprises two members of non-metallic material of which the surface admittance will vary with the redox activity of a medium in contact with the material, said members being electrically insulated one from the other.

In a preferred embodiment, the non-metallic members are supported by a probe body of generally elongate form for insertion into the vagina and conveniently made from an electrically insulating material such as plastics. The members of non-metallic material of varying surface admittance are conveniently embedded in the probe body, desirably at a position such that they may contact the posterior fornix when the probe is inserted into the vagina.

The non-metallic material may be a non-metallic semiconducting material, the surface admittance of which will vary with redox activity when in contact with a medium having redox activity. Examples of suitable semiconducting materials include doped silicon and peferably carbonaceous semiconducting materials such as carbon fibres or vitreous (or glassy) carbon. In general, the semiconducting material for in vivo use will be non-toxic and in this respect vitreous carbon is most preferred. A suitable vitreous carbon may be obtained from Le Carbone Lorraine of Gennevilliers, France. The use of the non-metallic material for the material of varying surface admittance is especially advantageous for in vivo use since this generally avoids any possibility of the release of metal ions in use, in contrast to prior art electrometric methods of detecting changes in vaginal fluids.

Vitreous or glassy carbon has also been found to be particularly useful for the construction of the probe since it has been found that this material is especially sensitive to changes in redox activity, as well as exhibiting favourable biocompatibility.

Means are conveniently provided for applying a transient or time varying potential, generally of low voltage (e.g. 50–500 mv), across the two members and to provide an indication of the electrochemical admittance of the probe, which is itself a function of the redox activity of the medium contacting the probe. The use of the dynamic application of potential to the electrodes facilitates the determination of surface admittance. The means to provide an indiction of the surface admittance of the probe may, for example, comprise means for detecting and analysing the resultant current between the members, or means for detecting changes in the frequency of an oscillator means connected with the members.

In its simplest form the apparatus can be designed simply to display a value corresponding to the electrochemical admittance of the probe and which the user records on a daily basis. Just as a rise in the basal body temperature (BBT) can be used to indicate the onset of ovulation, so a drop in e.g. the measured current, indicating a decrease in the admittance of the probe, can be used to signal ovulation. In a more sophisticated arrangement the apparatus may include a memory for memorizing the daily values and for signalling automatically the onset of ovulation.

As will be apparent the apparatus of the present invention can be of a very small compact size and readily portable, requiring only quite low power batteries for operation, and the largest item being the probe itself. For accuracy, measurements should be made regularly each day and at the same time of day. Also the user should, so far as possible, take readings with the probe in exactly the same position each day. For example, for best results in detecting ovulation, it has been found that measurements should be taken throughout the menstrual cycle with the distal end of the probe located in the region of the posterior fornix, a region which, with a little practice, the user can locate regularly and without difficulty.

If desired, the apparatus according to the invention may include means for the detection of other physiological changes, e.g. changes in temperature, pH, chloride ion concentration or ATP concentration. Such means may be conveniently incorporated into the probe of the apparatus so that more than one physiological parameter can be measured at the same time. For example, in detecting ovulation greater accuracy may be achieved by monitoring both changes in redox activity and temperature during the menstrual cycle.

The invention will be further described with reference to the accompanying drawings, in which.

Figure 1A:
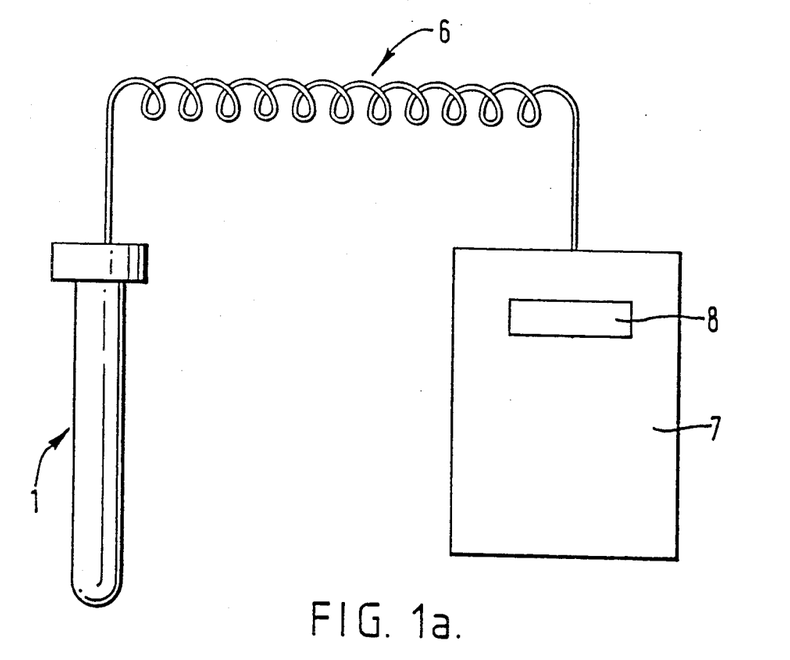
FIGS. 1a and 1b illustrate views of two ovulation predictor devices according to the invention.
Figure 1B:
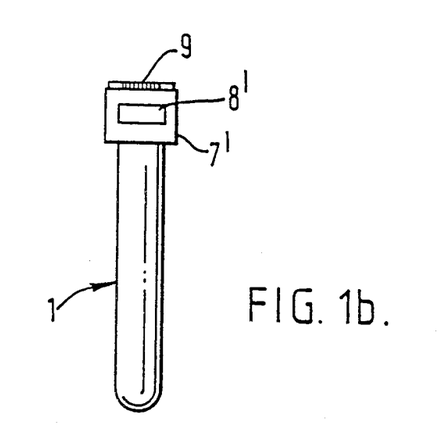

Referring to FIGS. 1a and 1b, the preferred application for apparatus in accordance with this invention is as an ovulation predictor or detector for human beings or animals. For these applications the apparatus comprises a vaginal probe body (1) shown in more detail in FIGS. 2a, 2b and 2c comprising a rigid or semi-rigid cylindrical element (approximately 10 cms in length and 1 cm in diameter for human use) having a rounded distal end insertable into the vagina, with the distal end extending therein into the region of the posterior cervical fornix. As shown in the detail of FIGS. 2a, 2b, 2c and 2d, the probe body (1) supports two electrodes or elements (2, 3) of glassy (vitreous) carbon separated by or embedded in an insulating element (4). The particular dimensions of the probe body will normally depend on its intended use. For example, where the probe is to be used with cattle, the probe body may be conveniently up to about 60 cms in length and about 3 cms in diameter.

Figures 2A, 2B:
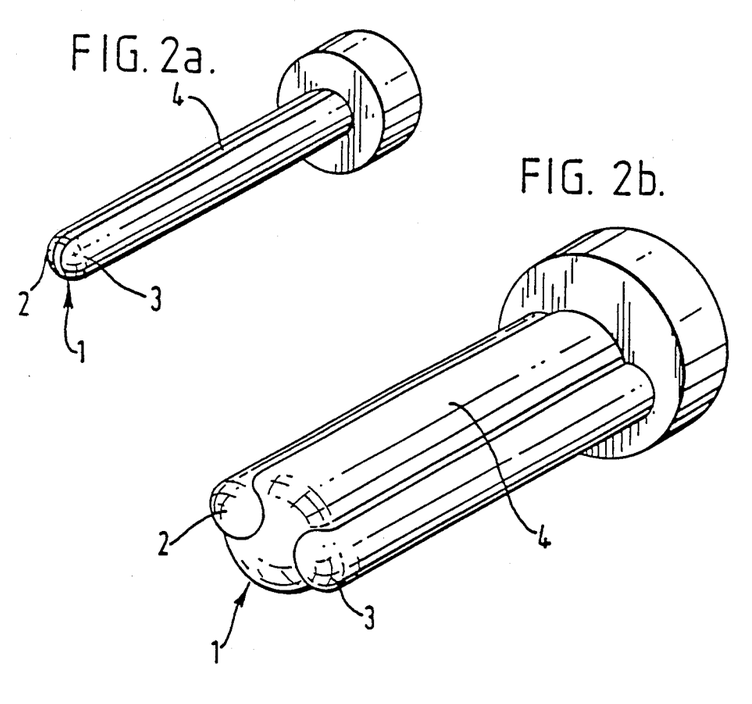
FIGS. 2a, 2b, 2c and 2d illustrate alternative probes for use with either of the devices of FIGS. 1a and 1b.
Figures 2C, 2D:
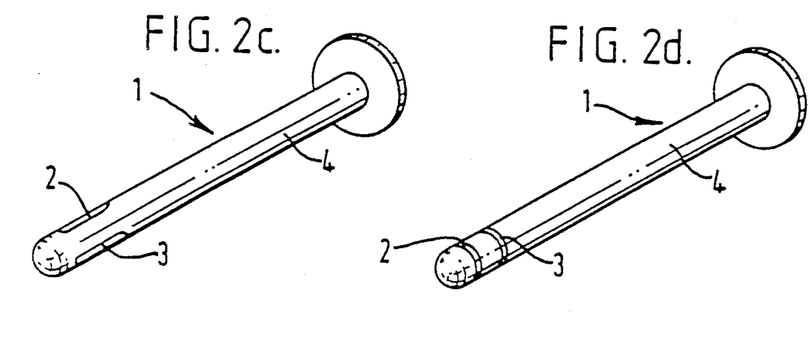

In FIG. 2a, the probe comprises two hemispherical section glassy carbon electrodes (2, 3) separated by a planar insulating layer (4), and in FIG. 2b, the probe comprises a substantially circular section insulating member (4) having two diametrically opposed grooves in which are seated the two electrodes (2, 3) each in the form of a circular section rod of vitreous carbon. In FIG. 2c, the two electrodes (2, 3) are positioned relatively closely over a generally small part of the probe body so as to enable measurement of changes in redox activity at selected points in the vagina. In FIG. 2d, the two electrodes (2, 3) are in the form of rings.

In one form of apparatus, shown in FIG. 1a, there is connected to the probe by means of a suitably flexible and extensible lead (6) a housing (7) adapted to contain dry cell batteries to power the probe and containing the electronic circuitry described hereinafter in more detail and required to detect the change in surface admittance of the two vitreous carbon electrodes of the probe when in an oxidation-reduction environment such as exists within the vagina. Also incorporated in the housing (7) is an appropriate visual display device (8), which can be either an analogue or digital display, and which can be used to display any of a range of signals depending upon the simplicity or complexity of the device. FIG. 1b shows an alternative form of the apparatus in which a housing (7') for a display device (8') and batteries is physically attached to the probe body (1). This provides a very compact unit, but because of the greater difficulty of reading the display in this arrangement, an audio indicator (9) is preferably provided to produce an audible indication when a steady reading has been achieved. In the simplest case the display device of either version can simply be a digital or analogue display of the current output from the probe when in situ. In more sophisticated arrangements, as already indicated, daily readings can be memorized and used to form the basis of a straightforward "fertile" or "non-fertile" signal.

Figure 3:
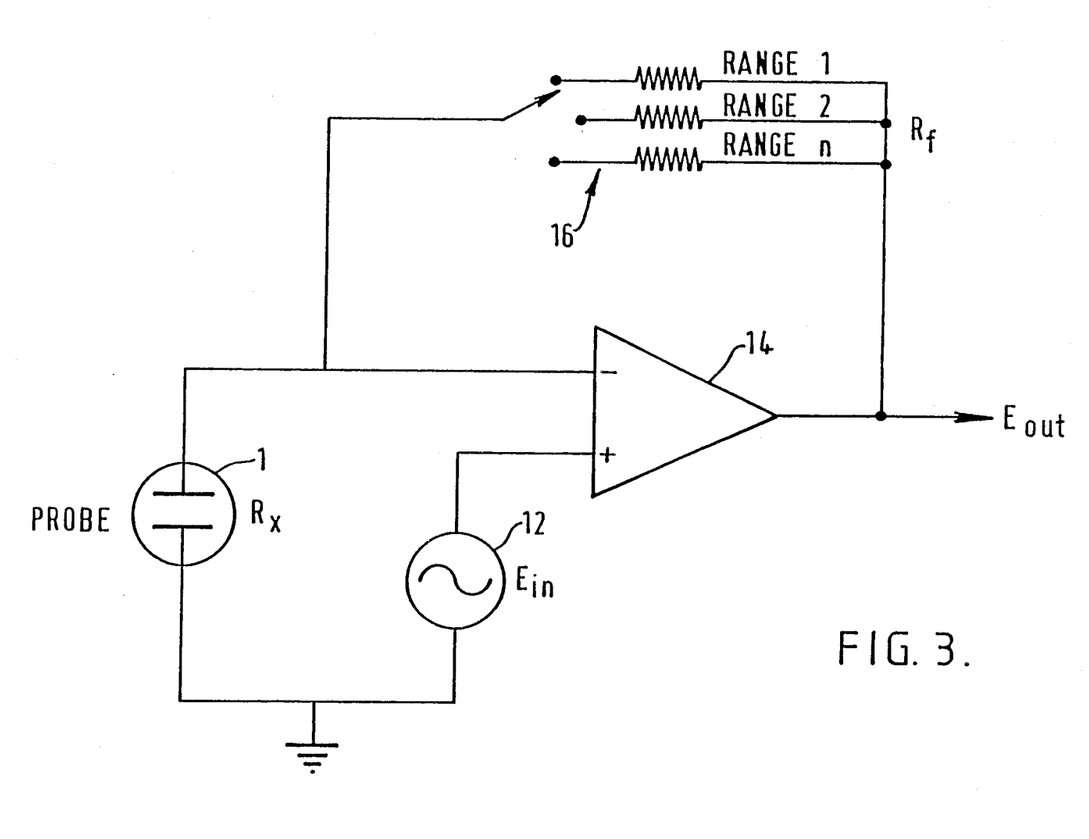
FIG. 3 is a schematic illustration of an electrical circuit connected to the probe.

FIG. 3 shows an exmaple of an electrical circuit for detecting changes in admittance at the probe (1). The probe (1) and an alternating voltage source (12) are shown each connected between a reference point (shown as earth) and respectively inverting and non-inverting inputs of an operational amplifier (14). The output of the operational amplifier (14) is fed back to the inverting input via a feedback path comprising a selectable resistor (16).

If the resistance of the probe (1) is $R_x$ and that of the selected resistor (16) is $R_f$, and the voltage of the alternating source (12) is $E_{in}$ and that of the output is $E_{out}$, it can be shown that $$E_{out} = E_{in}\left(\frac{R_f}{R_x} + 1\right)$$

If $R_f$ is substantially greater than $R_x$, this approximates to:

$$E_{out} = E_{in}\frac{R_f}{R_x}$$

Thus, since the admittance is inversely dependent on $R_x$, the output voltage will provide a directly proportional measure of the admittance.

For best results as an ovulation predictor the apparatus will be used by the user on a regular basis, preferably at the same time each day, e.g. first thing in the morning or last thing at night, and users will be recommended so far as possible to use the probe in exactly the same position on each occasion. Experimentally, the best results have been obtained using the probe twice daily, i.e. night and morning.

In a series of trials carried out using a probe constructed in accordance with FIG. 2c, a consistent pattern of results has been obtained illustrated by FIGS. 4-7.

In each case the probe was used regularly last thing at night by a healthy adult female and a record made of the measured output from the probe ($\mu$A) at various energisation levels. For comparison with a recognised, albeit imperfect known method for the detection of ovulation, the subject also measured and recorded her basal body temperature (BBT) using a commercial clinical thermometer inserted under the tongue, these measurements being made first thing in the morning before rising.

Figure 4:
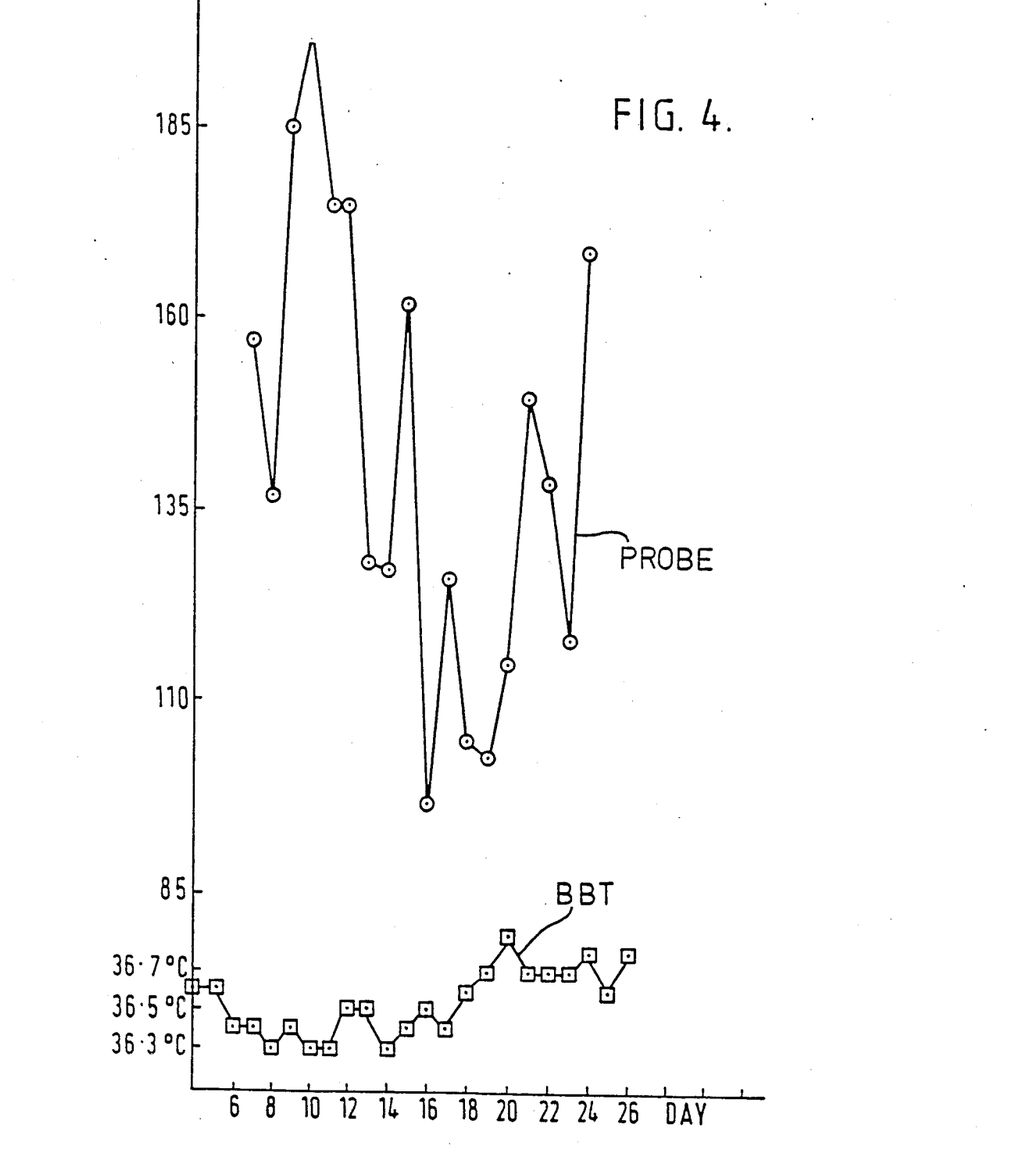
FIGS. 4–8 are graphs setting out results obtained using various probes constructed in accordance with this invention.
Figure 5:
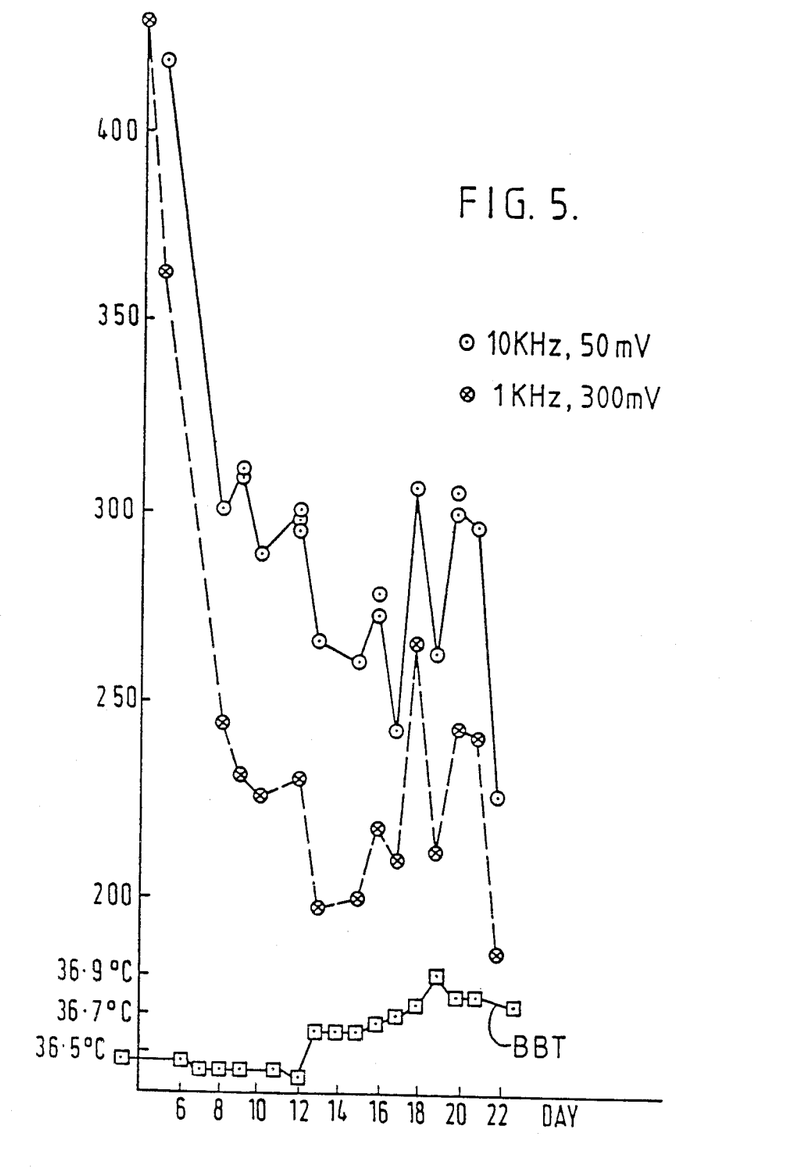
Figure 6:
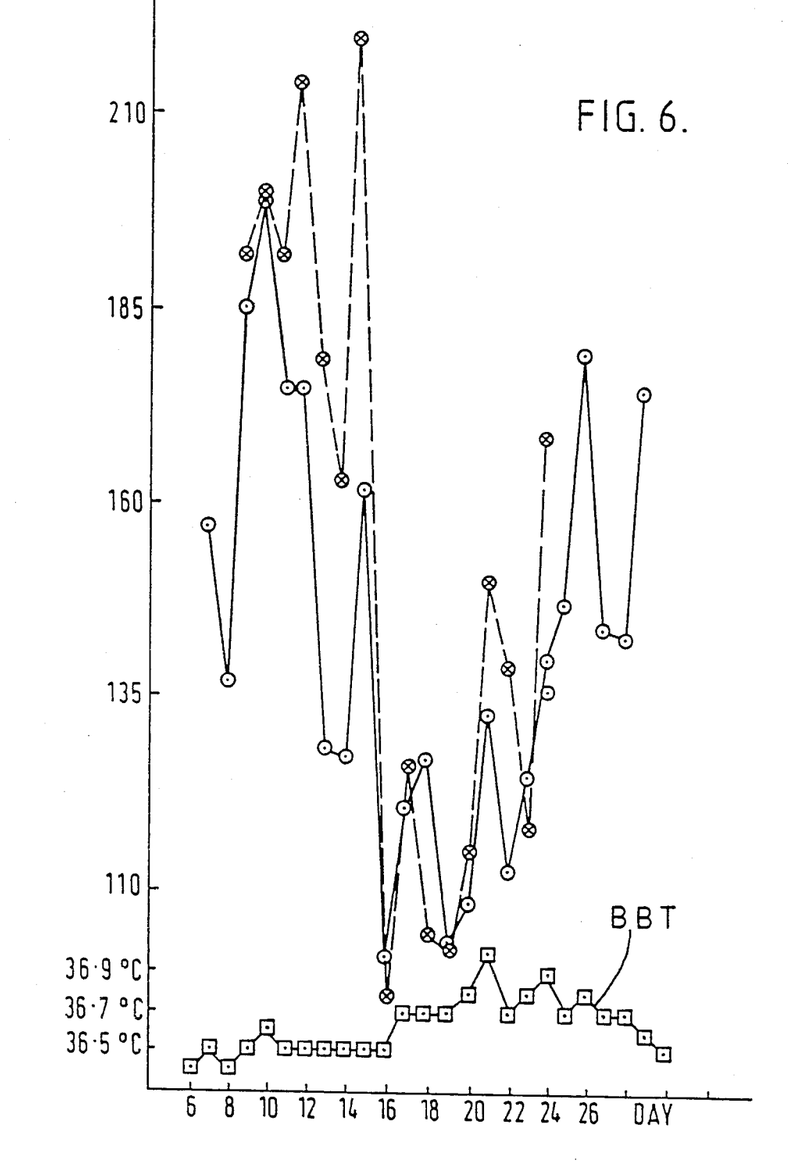

FIG. 4 illustrates the results obtained in a first series of tests with the probe operating at 10 kHz and 100 mV. FIG. 5 illustrates the results of two different series of tests with the probe operating at 10 kHz and 50 mV, and at 1 kHz and 300 mV. FIG. 6 illustrates the results from two successive tests carried out during successive cycles and clearly demonstrates the reproducibility of the pattern in the data.

Figure 7:
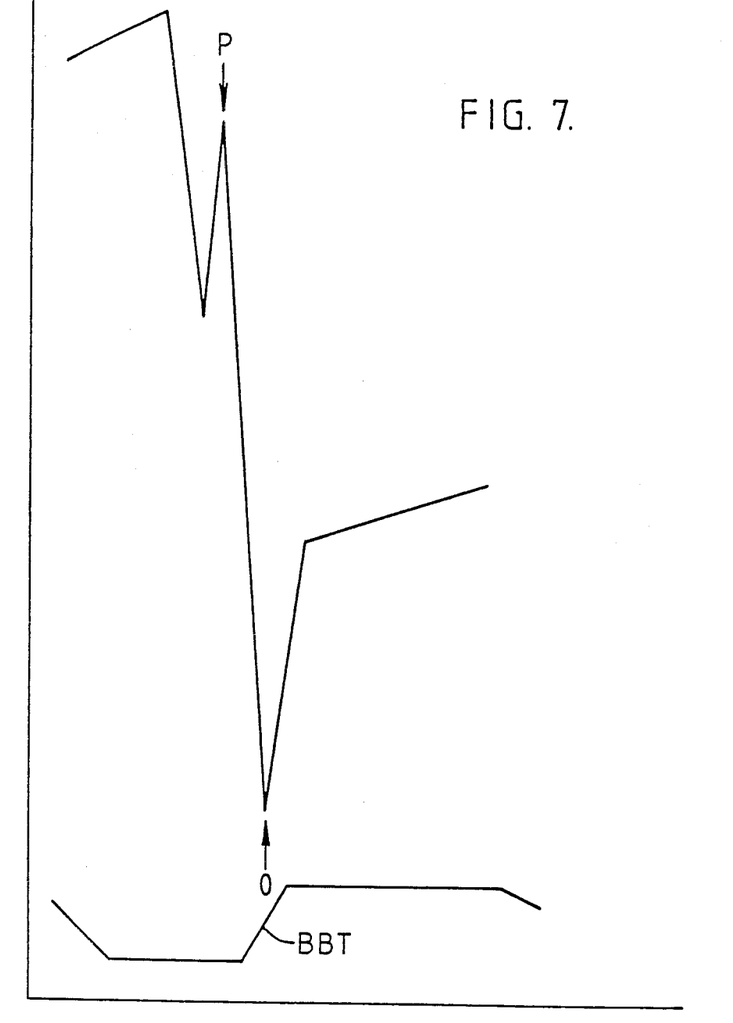
Figure 8:
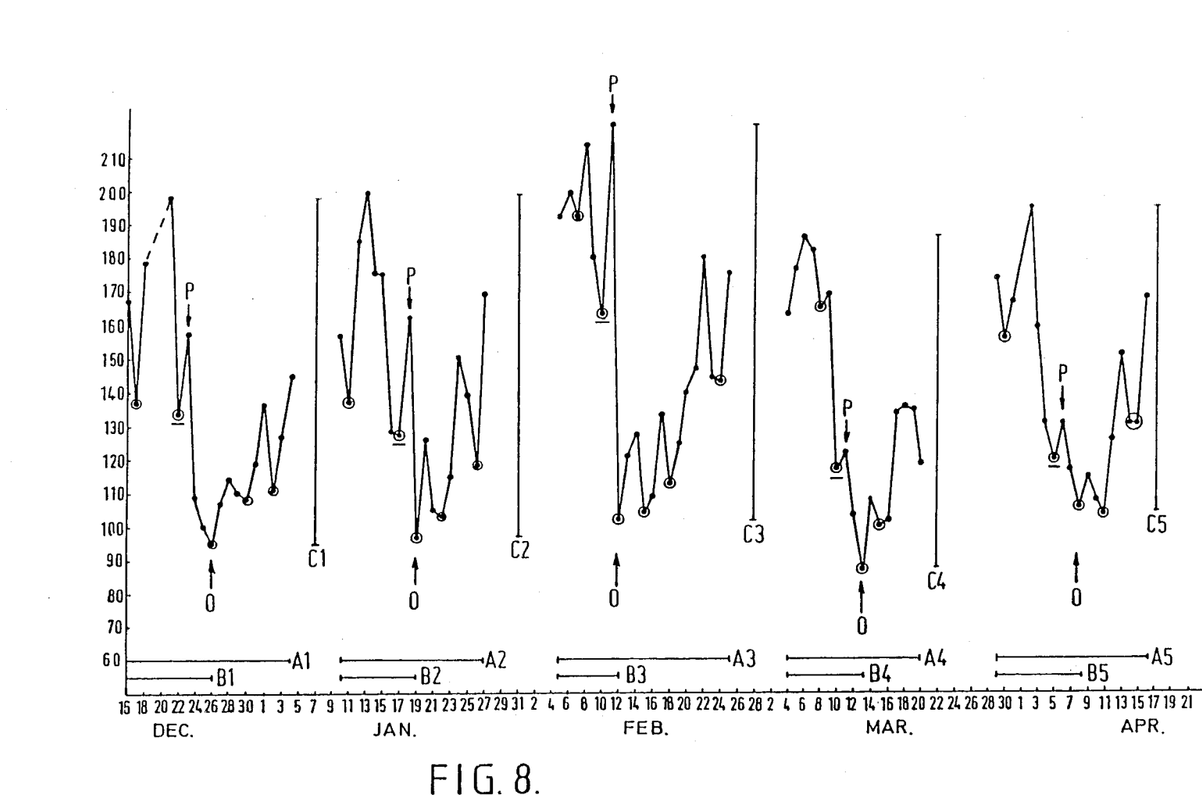

In each case a clear correspondence is established between the output current from the probe and the BBT, the output current showing a distinct dip (ovulation dip, O) coincident with the rise in BBT which is known to occur at about the time of ovulation. Even more characteristically the output curves show a distinct peak immediately preceding ovulation, and which can be referred to as the prediction peak (P). An idealised curve showing these two features, the prediction peak (P) and the ovulation dip (O) is shown in FIG. 7, and the results obtained from monitoring the subject over 5 cycles are shown in FIG. 8. These two features, the prediction peak (P) and the ovulation dip (O) are found to be quite characteristic of the output of the probes of this invention and it can be hypothesised that the ovulation dip (O) coincides with the known peak emission of luteinising hormone (LH) which is believed to initiate ovulation, whilst the predictor peak (P) can be indicative of an earlier hormonal change preceding the LH surge by 1 or 2 days. Indeed, the output from the probes of this invention shows a number of characteristic subsidiary peaks and dips both pre- and post-ovulation and which may provide further indications of other hormonal changes taking place in the body at various stages in the menstrual cycle.

Further experimental work using various differently sized probes has also shown that the size and location of the probe may have a significant effect on the response. Thus it is found that probes having a configuration such that there is contact with the vagina over a wide area, and not just in the region of the posterior cervical fornix, show response curves still having the predictor peak (PP) but showing a wider ovulation trough, rather than a sharp dip at ovulation, which is characteristic of probes configured to contact the posterior cervical fornix.

Figure 9:
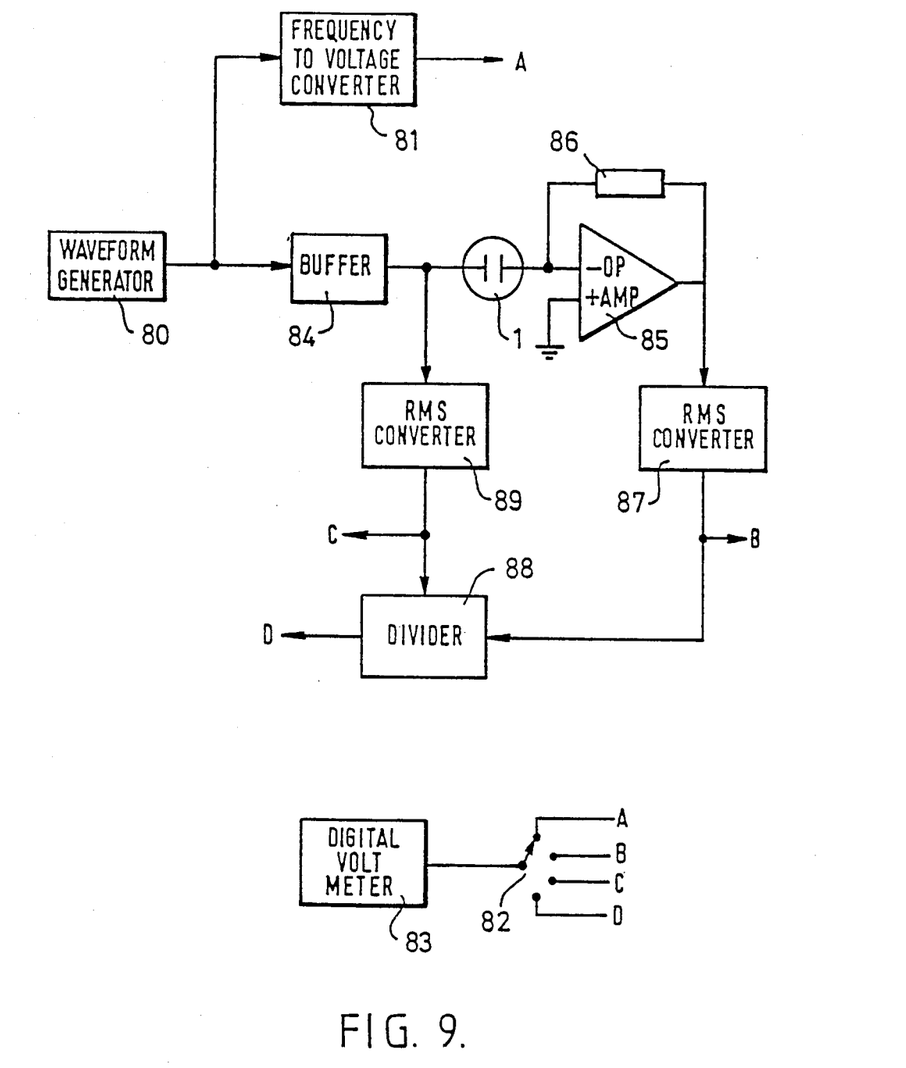
FIGS. 9 and 10 are two further electrical circuits usable with the probe.

FIG. 9 shows a circuit which is particularly useful for experimental work involving changes in frequency and voltage of the alternating input signal.

The probe (1) is again connected to the inverting input of an operational amplifier (85), but in this case the non-inverting input is connected to earth. A resistor (86) is connected in the feedback path between output and inverting input of the operational amplifier (85).

The alternating voltage is derived from a waveform generator (80) fed to the probe (1) via a buffer amplifier (84). RMS converters (89, 87) receive respectively the input voltage to the probe (1) and the output voltage of the amplifier (85), and provide voltages which are the root mean squares of the respective alternating voltages. The outputs of the RMS converters (89, 87) are fed to a divider (88). A frequency to voltage converter (81) receives the output of generator (80) and itself provides an output A. Outputs B, C and D are derived from the RMS converters (87, 89) and the divider (88) respectively. The outputs A, B, C and D can be selectively connected via a switch (82) to a digital voltmeter (83).

The divider (88) divides $E_{out}$ by $E_{in}$ and therefore removes the constant or proportionality which is dependent on the input voltage. Accordingly, the output D provides a voltage independent of input voltage variations. Output A is a measure of the frequencies, and outputs B and C are measures of the output ($E_{out}$) and input ($E_{in}$) voltages respectively.

Figure 10:
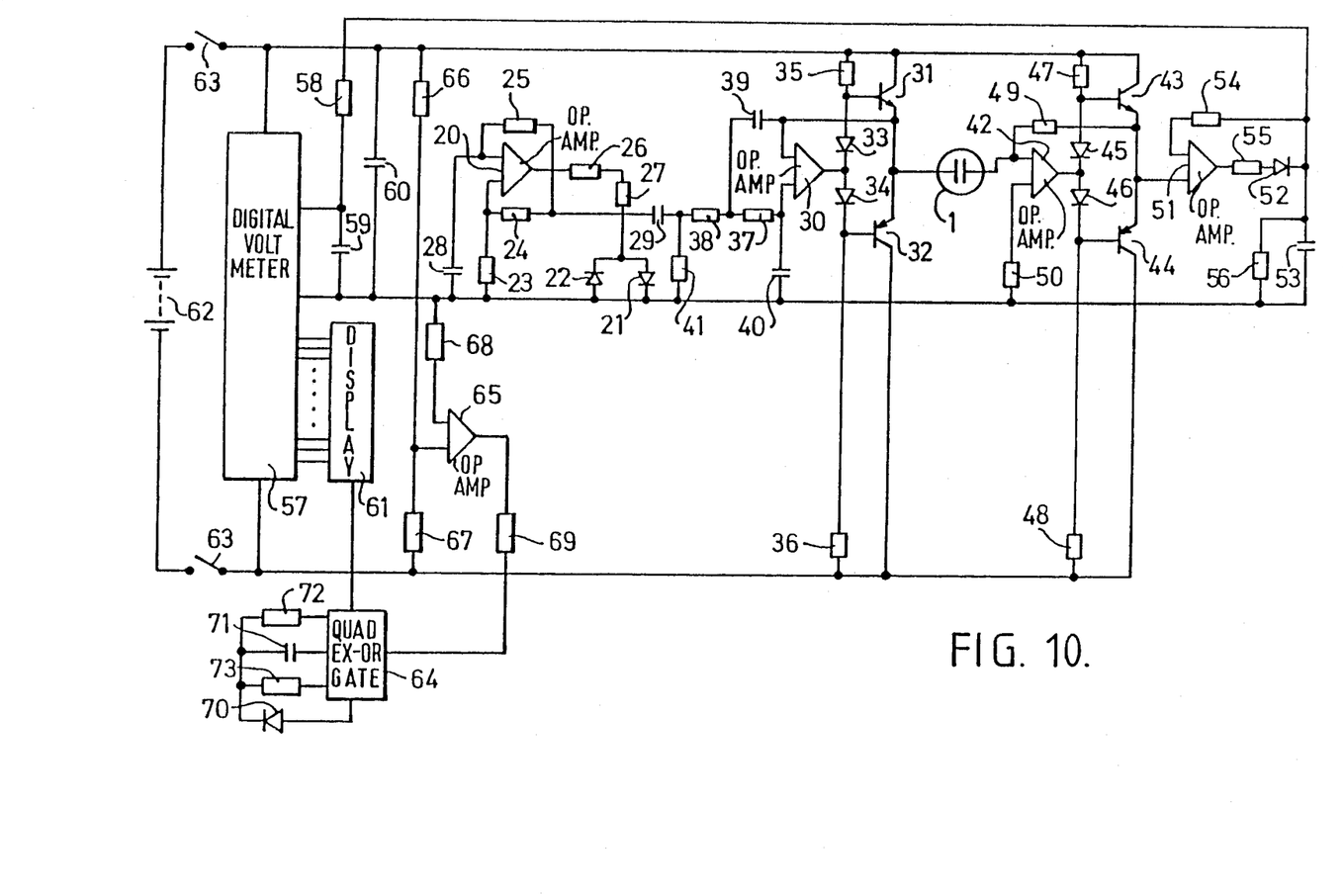

FIG. 10 is a more detailed circuit diagram of a detection circuit suitable for use with the apparatus according to the invention. It will be seen that the configuration of probe (1) and operational amplifier (42) is broadly similar to that of FIGS. 3 and 9, but with respect to the latter, the FIG. 10 circuit only provides an indication of the output voltage and hence probe admittance; no other test voltages are to be measured. Referring to FIG. 10, a waveform generator is constituted by an operational amplifier (20) and its associated components. An operational amplifier (30) acts as a buffer receiving the output signal from the waveform generator and supplying the signal to the probe (1). The output signal from the probe (1) is fed via the operational amplifier (42) to an RMS converter formed by an operational amplifier (51) and its associated components. The RMS converted output signal is fed via a resistor (58) to a measuring input of a digital voltmeter (57). The digital voltmeter (57) is provided with a display (61) which receives a display drive input from a quad EX-OR gate circuit (64) and associated diode (70), capacitor (71) and resistors (72), (73). The circuit of FIG. 10 is operative to modify the output signal from the waveform generator in dependence on the admittance of the probe (1), and this modified output signal appears as a steady state signal at the output of the RMS converter formed by the operational amplifier (51); this steady state signal is then measured by the digital voltmeter (57).

Another significant feature of the detection aspect as previously described is that the obtained response using the probes of the present invention is a drop in current output, not an increase, which was to be expected had the known preovulation increase in conductivity of the cervical mucus have been a major factor in the function of the probe of the present invention. Thus the decrease in output current is consistent with the hypothesis that it is variations in the surface admittance of the material of the probe in response to changing redox potentials in the cervical mucus that provides the modus vivendi of the present invention, although it is not intended that the scope of this invention should in any way be restricted by hypothetical or theoretical explanation.

A further generally important feature of the invention, particularly so far as in vivo use in humans is concerned, is that the probe is constructed entirely of non-metallic, biocompatible materials which is important from two points of view, one physiological and the other electrochemical. The biochemical inertness of the probe means that it can be used repeatedly without any risk to the user, and provided that a few elementary hygiene and sanitary precautions are taken, without any substantial risk of introducing infection. Secondly, in the absence of any exposed metallic part, e.g. electrodes, there are no extraneous chemical or electrochemical reactions to worry about either from the physiological viewpoint (it being known, for example, that many metal ions are toxic) or from the technical, electrochemical viewpoint such as side electrolytic or polarisation reactions which might otherwise occur and adversely affect the probe measurements.

Thus the present invention is believed to provide a completely safe, aesthetically acceptable and effective portable apparatus for the prediction and detection of ovulation in humans and animals, and which can be used effectively by unskilled, untrained users. In addition to the prediction and detection of ovulation in humans and animals, it is also believed that the method and apparatus of the present invention may be used in vitro or in vivo to detect other conditions which result in either temporary or permanent changes in redox activity, e.g. early pregnancy detection and/or detection of cervical cancer and other vaginal pathologies.

What is claimed is:

1. A method of monitoring changes of redox activity in a medium in vitro or in vivo which comprises placing into said medium a probe having a plurality of non-metallic electrodes exposed to said medium and whose surface admittance varies inversely with the reductive activity in said medium, and detecting the resulting changes in said surface admittance.

2. A method according to claim 1 wherein changes in surface admittance are detected by applying a time-varying electrical potential of low amplitude and high frequency to said electrodes and monitoring the resultant current between the electrodes.

3. Apparatus for monitoring changes of redox activity in vitro or in vivo which comprises a probe introducible into a medium, said probe having a plurality of electrodes composed of non-metallic material and whose admittance varies inversely with the reductive activity in said medium, and means for detecting andy resulting changes in said surface admittance.

4. Apparatus according to claim 3 wherein each of said electrodes is composed of substantially identical material.

5. Apparatus according to claim 3 wherein said probe includes two electrodes.

6. Apparatus according to claim 3 wherein said electrodes are composed of a non-metallic semiconducting material.

7. Apparatus according to claim 3 wherein said electrodes are composed of vitreous carbon.

8. Apparatus according to claim 3 wherein said means for detecting changes in surface admittance includes means for applying a time-varying electrical potential of low amplitude and high frequency to said electrodes and means for monitoring resultant current between said electrodes.

9. Apparatus according to claim 3 in which said probe is insertable into the vagina of a mammal to be examined, and including means for measuring the surface admittance of the probe when in situ in the vagina, said means for measuring coupled to said means for detecting, whereby said apparatus functions as an ovulation predictor and/or detector for mammals.

10. Apparatus according to claim 9 wherein said probe comprises an elongated element insertable into the vagina and having two of said electrodes, said probe further comprising means disposed between said to electrodes for electrically insulating said electrodes from each other, said means for detecting including means for applying a time-varying potential across said electrodes when in situ in the vagina, and said apparatus including means coupled to said means for measuring for providing an indication of the surface admittance of said electrodes.

11. Apparatus according to claim 10 wherein said means for detecting any resultant changes in surface admittance comprises means for detecting current flow between said electrodes resulting from said time-varying potential across electrodes, and means for analyzing said current flow.

12. Apparatus according to claim 11 further including a visual display device coupled to said means for measuring whereon results are displayed visually as an indication of the onset of ovulation.

* * * * *